United States Patent [19]
Sobicinski

[11] Patent Number: 5,786,366
[45] Date of Patent: Jul. 28, 1998

[54] METHOD AND APPARATUS FOR REHYDRATING DRY SKIN

[76] Inventor: J. Daniel Sobicinski, 191 Wierimus La., Hillsdale, N.J. 07642

[21] Appl. No.: 787,540

[22] Filed: Jan. 22, 1997

[51] Int. Cl.⁶ .......................... A61K 31/47; A61K 31/22
[52] U.S. Cl. ........................................... 514/312; 514/546
[58] Field of Search ................................... 514/311, 312, 514/546

[56] References Cited

U.S. PATENT DOCUMENTS 4,788,061  11/1988  Shore ....................................... 424/448

FOREIGN PATENT DOCUMENTS 0191128  8/1986  European Pat. Off. .

*Primary Examiner*—Phyllis G. Spivak
*Attorney, Agent, or Firm*—Aquilino & Welsh

[57] ABSTRACT

A method for rehydrating dry skin of an individual is disclosed. In accordance with the method, a balm of lanolin and hydroxyquinoline sulfate is first applied to the skin surface to be treated, wherein the skin surface is a hand or a foot of an individual. The skin surface is then covered with a cotton cover, and the cover is maintained over the skin surface for a predetermined period of time. The cover is then removed to reveal the rehydrated skin surface. A kit for practicing the invention is also provided.

8 Claims, 3 Drawing Sheets

5,786,366

METHOD AND APPARATUS FOR REHYDRATING DRY SKIN

BACKGROUND OF THE INVENTION

1. Field of the Invention

The invention relates to a method and kit for treating dry skin. More particularly, the invention relates to a method and kit for rehydrating dry skin of an individual by applying a balm to an affected skin surface and covering the skin surface with a cover for a predetermined period of time.

2. Description of the Prior Art

Individuals are consistently confronted with the problem of rehydrating dry skin in a convenient manner. If an individual's skin is not promptly and properly moisturized, the affected skin often becomes damaged; that is, the skin may peel, crack, and ultimately bleed.

Most often, people treat dry skin by applying a moisturizing agent directly on the affected skin and rubbing the moisturizing agent into the skin. Unfortunately, once the moisturizing agent is applied to the affected skin, the affected skin remains exposed to the environmental conditions which caused the dry skin in the first place. As a result, much of the moisturizing agent is not absorbed by the affected skin. This limits the effectiveness of the moisturizing agent. An individual must, therefore, continually apply the moisturizing agent to his or her hands throughout the day.

The limitations of simply applying moisturizing agent to the affected skin become especially problematic when an individual's skin is severely dehydrated and requires immediate, effective treatment. In these instances, the affected skin may remain damaged for many days before enough moisturizing agent is absorbed by the affected skin to fully rehydrate the damaged skin.

After studying the limitations associated with the application of traditional moisturizing agents, it is apparent that a need exists for a method by which individuals may effectively and conveniently treat dehydrated skin. The present invention provides such a method, as well as a kit for performing the method.

SUMMARY OF THE INVENTION

It is, therefore, an object of the present invention to provide a method for rehydrating dry skin of an individual. In accordance with the method, a balm is first applied to the skin surface to be treated, wherein the skin surface is a hand or a foot of an individual. The skin surface is then covered with a cover, and the cover is maintained over the skin surface for a predetermined period of time. The cover is then removed to reveal the rehydrated skin surface.

It is also an object of the present invention to provide a method for rehydrating dry skin wherein the skin surface is the hand of an individual.

It is another object of the present invention to provide a method for rehydrating dry skin wherein the cover is a glove shaped and sized to fit over the hand of an individual.

It is a further object of the present invention to provide a method for rehydrating dry skin wherein the glove is a cotton glove.

It is also an object of the present invention to provide a method for rehydrating dry skin wherein the skin surface is the foot of an individual.

It is another object of the present invention to provide a method for rehydrating dry skin wherein the cover is a sock shaped and sized to fit over the foot of an individual.

It is a further object of the present invention to provide a method for rehydrating dry skin wherein the sock is a cotton sock.

It is also an object of the present invention to provide a method for rehydrating dry skin wherein the balm is applied before an individual goes to sleep and the skin surface is covered by the cover while the individual sleeps.

It is another object of the present invention to provide a method for rehydrating dry skin wherein the balm is a blend of lanolin and hydroxyquinoline sulfate in a moisturizing base formula.

It is a further object of the present invention to provide a kit for rehydrating dry skin. The kit includes a rehydrating balm to be applied to a skin surface being treated and a cover for covering the skin surface. The cover is adapted to be maintained over the skin surface for a predetermined period of time, and wherein the rehydrating balm is applied to the skin surface and covered by the cover for a predetermined period of time during which the skin surface is rehydrated.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching one skilled in the art how to make and/or use the invention.

Figure 1:
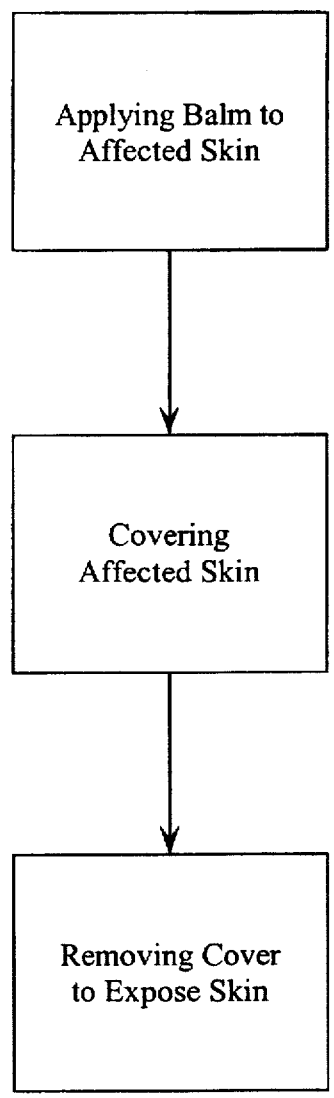
FIG. 1 is a flow chart outlining the present method.

With reference to FIG. 1, the present method is outlined. The method is an effective treatment for dehydrated (that is, dry) and chapped skin. The method will now be described for use on the hands of an individual. However, it should be understood that the invention may be practiced on a variety of skin surfaces, including the feet of an individual. The method is practiced by first applying a balm to the dry and chapped skin on the hands of an individual. The balm is preferably LANSULATUM™. LANSULATUM™ is a moisturizing formula manufactured and sold by NORSTAR CPC., Inc. LANSULATUM™ provides a blend of lanolin and hydroxyquinoline sulfate 0.15% in a moisturizing base formula.

The LANSULATUM™ balm is manufactured by first adding 3.5 lbs. of multiwax to 326.5 lbs. of petrolatum. The mixture of petrolatum and wax is then melted. 5.6 oz. of propyl paraben is then added to the hot drum containing the petrolatum and the wax. 5.6 oz. of hydroxyquinoline sulfate is next dissolved in 54 oz. of hot water and 17 lbs. 10 oz. of lanolin is melted in a stainless steel bucket. The hydroxyquinoline sulfate/water mixture is then mixed with the melted lanolin. The lanolin mixture is then added to the petrolatum/wax/propyl paraben mixture and the two mixtures are mixed well. 2.82 oz. of almond oil is then added to the mixture to complete the preparation of the balm. Before the balm is packaged and labeled, a sample of the balm is tested to ensure quality control.

After the balm is applied to the hands of an individual, white cotton gloves are placed over the individual's hands. The gloves are maintained on the individual's hands for a predetermined period of time. In accordance with the preferred embodiment of the present invention, the balm is applied before going to bed and the gloves remain on the individual's hands while the individual sleeps.

When the individual awakes, or after a predetermined period of time has passed, the individual removes the gloves. If the individual's hands are sufficiently rehydrated, the process is complete. If, however, additional treatments are required, the process is repeated for three consecutive nights, or as needed.

As discussed above, the invention may be practiced on body parts other than the hands of an individual, without departing from the spirit of the present invention. Where the invention is practiced on the feet of an individual, the balm is applied to the individual's feet and socks are positioned over the treated feet for a predetermined period of time.

Figure 2:
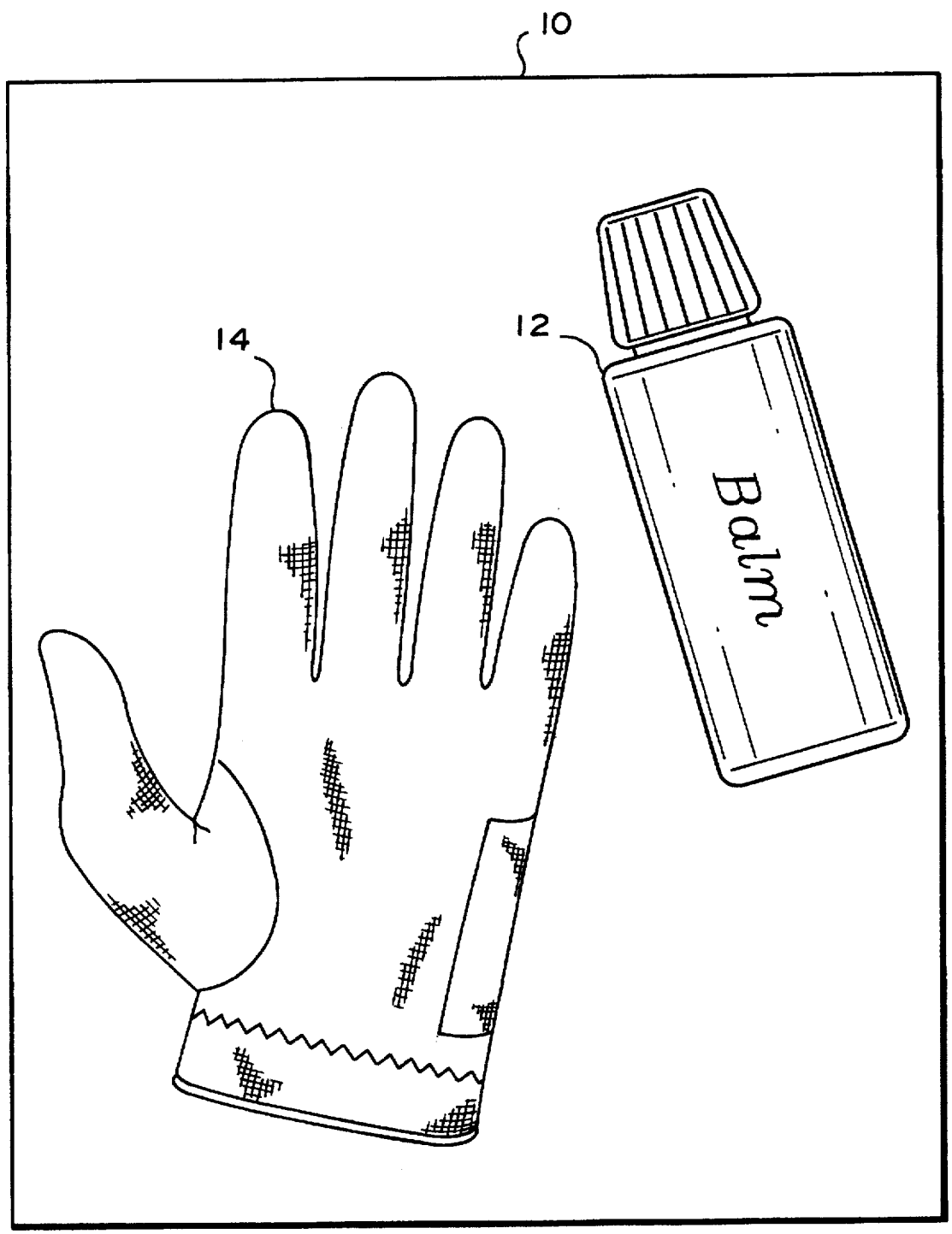
FIG. 2 is a perspective view of a kit for practicing the present method on the hands of an affected individual.
Figure 3:
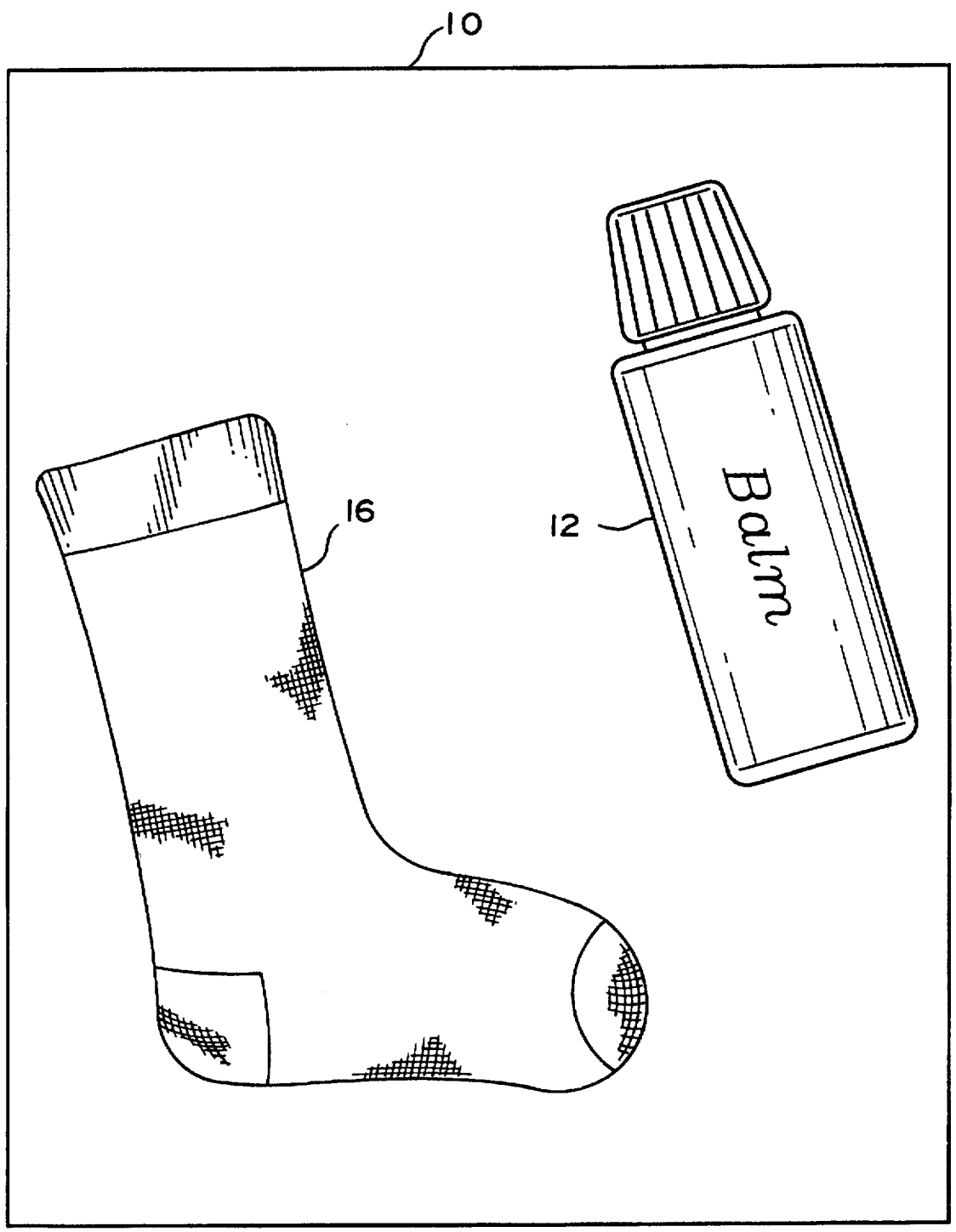
FIG. 3 is a perspective view of a kit for practicing the present method on the feet of an affected individual.

In accordance with the present invention, a kit 10 is provided for practicing the method described above. With reference to FIGS. 2 and 3, the kit 10 includes a rehydrating balm 12 to be applied to a skin surface being treated, such as the hands or feet of an individual. The kit also includes a cover for covering the skin surface. Where the skin surface is the hands of the individual, the cover is a white cotton glove(s) 14, and where the skin surface is the feet of an individual, the cover is a white cotton sock(s) 16.

While the preferred embodiments have been shown and described, it will be understood that there is no intent to limit the invention by such disclosure, but rather, is intended to cover all modifications and alternate constructions falling within the spirit and scope of the invention as defined in the appended claims.

I claim:

1. A method for rehydrating dry skin of an individual, comprising the following steps:

applying a balm of lanolin and hydroxyquinoline sulfate in a moisturizing base formula to a skin surface to be treated, wherein the skin surface is a hand or a foot of an individual;

covering the skin surface with a cover, wherein the cover is a cotton glove or sock shaped to respectively fit over the hand or foot of the individual;

maintaining the cover over the skin surface for a predetermined period of time; and removing the cover to reveal a rehydrated skin surface.

2. The method according to claim 1, wherein the skin surface is the hand of an individual.

3. The method according to claim 2, wherein the cover is a glove shaped and sized to fit over the hand of an individual.

4. The method according to claim 1, wherein the skin surface is the foot of an individual.

5. The method according to claim 4, wherein the cover is a sock shaped and sized to fit over the foot of an individual.

6. The method according to claim 1, wherein the balm is applied before an individual goes to sleep and the skin surface is covered by the cover while the individual sleeps.

7. A kit for rehydrating dry skin on the hands of an individual, comprising:

a rehydrating balm of lanolin and hydroxyquinoline sulfate in a moisturizing base formula to be applied to a hand of an individual;

a cotton glove for covering the hand of the individual, wherein the glove is adapted to be maintained on the hand for a predetermined period of time; and wherein the rehydrating balm is applied to the hand and covered by the glove for a predetermined period of time during which the hand is rehydrated.

8. A kit for rehydrating dry skin on the feet of an individual, comprising:

a rehydrating balm of lanolin and hydroxyquinoline sulfate in a moisturizing base formula to be applied to a foot of an individual;

a cotton sock for covering the foot of the individual, wherein the sock is adapted to be maintained on the foot for a predetermined period of time; and wherein the rehydrating balm is applied to the foot and covered by the sock for a predetermined period of time during which the foot is rehydrated.

* * * * *